(12) United States Patent
Schneider et al.

(10) Patent No.: US 6,333,021 B1
(45) Date of Patent: *Dec. 25, 2001

(54) MICROCAPSULES, METHOD OF MAKING AND THEIR USE

(75) Inventors: Michel Schneider, Troinex (CH); Philippe Bussat, Collonges-sous-Saleve (FR)

(73) Assignee: Bracco Research S.A., Carouge (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/555,147

(22) Filed: Nov. 8, 1995

(30) Foreign Application Priority Data

Nov. 22, 1994 (EP) .................................................. 94810660

(51) Int. Cl.⁷ ........................................................ A61B 8/00
(52) U.S. Cl. ............................................................ 424/9.52
(58) Field of Search .................................. 424/9.5, 9.51, 424/9.52, 489, 502, 498; 600/458, 441

(56) References Cited

U.S. PATENT DOCUMENTS

| | | | |
|---|---|---|---|
| 5,215,680 | * 6/1993 | D'Arrigo | 252/307 |
| 5,498,421 | * 3/1996 | Grinstaff et al. | 424/450 |
| 5,542,935 | * 8/1996 | Unger et al. | 604/190 |

FOREIGN PATENT DOCUMENTS

| | | |
|---|---|---|
| 0 458 745 A1 | 11/1991 | (EP) . |
| 0 467 031 A3 | 1/1992 | (EP) . |
| 0 535 387 A1 | 4/1993 | (EP) . |

* cited by examiner

*Primary Examiner*—Michael G. Hartley
(74) *Attorney, Agent, or Firm*—Nixon & Vanderhye

(57) ABSTRACT

The invention relates to microcapsules to a microcapsule with a mean size from a fraction of micrometer to 1000 micrometers having a biodegradable membrane encapsulating a gas core. The membrane comprising one or more biodegradable water insoluble lipids or mixtures thereof and optionally mixtures of the lipids with up to 75% by weight of biodegradable polymers encapsulates the core which is filled with air or a gas. Microcapsules disclosed, may be non-coalescent, dry and instantly dispersible, when in suspension in a physiologically acceptable carrier are useful as delivery vehicles for therapeutically active agents and/or as contrast agents for echographic imaging of organs of human or animal body. The microcapsules of the invention are made by a method in which a water-in-oil emulsion is made from an organic solution comprising dissolved a mono-, di-, triglyceride preferably tripalmitin or tristearin and optionally therapeutically active substance and an aqueous solution containing a surfactant, optionally evaporating part of the solvent, adding a redispersing agent and freeze drying the mixture. The freeze dried mixture is then redispersed in an aqueous carrier to separate microcapsules from debris and the semi-spherical or spherical microcapsules are dried.

21 Claims, 4 Drawing Sheets

US 6,333,021 B1

MICROCAPSULES, METHOD OF MAKING AND THEIR USE

TECHNICAL FIELD

The invention relates to microcapsules with a mean size from a fraction of micrometer to 1000 micrometers having a biodegradable membrane encapsulating air or gas filled core. The microcapsules disclosed may be non-coalescent, dry and instantly dispersible. The invention concerns a method of making the microcapsules and their use for delivery of therapeutically and/or diagnostically active substances. When in suspension in a physiologically acceptable carrier the microcapsules are useful as delivery vehicles for therapeutically active agents and/or as contrast agents for echographic imaging of organs of human or animal body. The invention also concerns a method of making ultrasound contrast agents using the microcapsules.

BACKGROUND ART

Recognition of the advantages obtained by the targeting and/or the controlled release delivery of therapeutic and diagnostic agents has inspired a lot of research and development of a variety of carrier systems. These range from a general purpose controlled or sustained release systems to systems which are specifically designed to suit a particular application. Depending on the type and nature of the active substance involved, numerous systems for the delivery of antibiotics, vitamins, proteins, etc. have been developed. A number of different carrier materials, from alginate or agar beads and phospholipid coatings or liposomes to very sophisticated polymeric materials, are known or currently in use for the encapsulation of active substances. However, many of the known systems are either too specific, i.e. dedicated to a single substance or at most to a single class of substances, and therefore are of little help when different active substances are considered. Being specifically chosen to carry a specific substance, many of the known delivery vehicles do not provide sufficient flexibility in modifying their release characteristics or biodegradability. Any changes of the nature of the carrier and/or the active to inactive ingredient ratio inevitably requires additional experimentation.

Furthermore, systems known so far do not lend themselves to the production of floating microparticles or floating tablets which can carry different active ingredients. They neither provide for convenient coupling of different functions or incorporation of different active substances within the same microcapsule, such as for example incorporation of a therapeutically active ingredient in the outer encapsulating membrane and a diagnostically active ingredient in the core; nor do they provide of-the-shelf biodegradable microcapsules which could be filled at convenience with a suitable medication in a suitable amount.

EP-A-0 458 745 (Sintetica) discloses air- or gas-filled microballoons bound by an interfacially deposited biodegradable membrane. These microballoons are usable as very efficient sound reflectors in the echographic imaging of body cavities and the blood stream. For preparing the microballoons, a filmogenic polymer is dissolved in a mixture of volatile organic solvents and the resulting organic solution mixed with an aqueous carrier phase to produce an oil-in-water emulsion. The emulsion is then treated, for instance by evaporation or insolubilization, such that the polymer precipitates and deposits to form a membrane at the droplet water/solution boundary. The organic solvent in the microballoons is eventually evacuated and, by lyophilising the suspension, the solvent in the microballoons is replaced by air or a gas. In order to increase their hydrophobicity the microballoons made from biodegradable polymers may contain up to 20% of fats, waxes and high molecular weight hydrocarbons.

U.S. Pat. No. 4,684,479 (D'Arrigo) discloses stabilised bubble suspensions, useful for ultrasound echographic measurements for different applications including echocardiography. The suspensions are formed by vigorously shaking in the presence of air (foaming) mixtures of surfactants with water or mineral oil. The mixtures of surfactants include (a) fatty acid monoglycerides, (b) esters of aromatic acids (like benzoic, phenylacetic, phthalic, salicylic acids, etc.) with sterols (like cholesterol, ergosterol, lanosterol, phytosterol, etc.), (c) a component from the group consisting of sterols, terpenes, bile acids and alkali metal salts of bile acids; and, optionally, (d) sterol esters of aliphatic acids, and (e) a member of the group consisting of glycerol and di- and triglycerides (e.g. dilaurin, trilaurin, dipalmitin, tripalmitin, distearin, tristearin, dimyristin, trimyristin, and the like).

WO-A-93/02712 (Danbiosyst) discloses solid microspheres or hollow (gas or vapour filled) amylodextrin microcapsules prepared by forming a shell from a water soluble starch derivative around a solid or liquid core and subsequently removing the core. The core may be a volatile oil such as perfluorohexane. The microcapsules may be made by an oil-water-oil double emulsion followed by chemical or heat hardening. The microcapsules can be used for echocardiography.

SUMMARY OF THE INVENTION

Briefly summarised, the invention relates to a solid microcapsule with a mean size from a fraction of micrometer to 1000 micrometers (1 mm) having a biodegradable lipidic membrane encapsulating air or gas core. The lipidic membrane comprises one or more biodegradable water insoluble, at room temperature solid, lipids or a mixture of biodegradable water insoluble lipids selected from mono-, di- or triglycerides, fatty acids, fatty acid esters, sterols, waxes and mixtures thereof. Mono-, di-, tri-myristin, -palmitin and -stearin are particularly useful, however, tripalmitin and tristearin are preferred. Non-coalescent, dry and instantly dispersible, the microcapsules when in suspension in a physiologically acceptable carrier are useful as delivery vesicles for therapeutically active substances and/or as ultrasound contrast agents. Optionally, the lipidic membrane may contain up to 75% by weight of biodegradable polymers.

Injectable compositions comprising a suspension of an effective amount of microcapsules of the invention in a pharmaceutically acceptable liquid carrier with usual additives and stabilisers useful as therapeutic and/or contrast agents are also disclosed.

The microcapsules of the invention are made by making a oil-in-water emulsion from an organic solution comprising, dissolved, a mono-, di-, tri-glyceride or a mixture thereof and an aqueous solution optionally containing a surfactant; optionally evaporating a part of the solvent, adding a redispersing agent and freezing the mixture obtained. The frozen mixture is then lyophilised to produce quasi-spherical or spherical microcapsules.

A method of making an ultrasound contrast agent by suspending the microcapsules (microballoons) in a physiologically acceptable carrier phase is also disclosed.

DETAILED DESCRIPTION OF THE INVENTION

Figure 1:
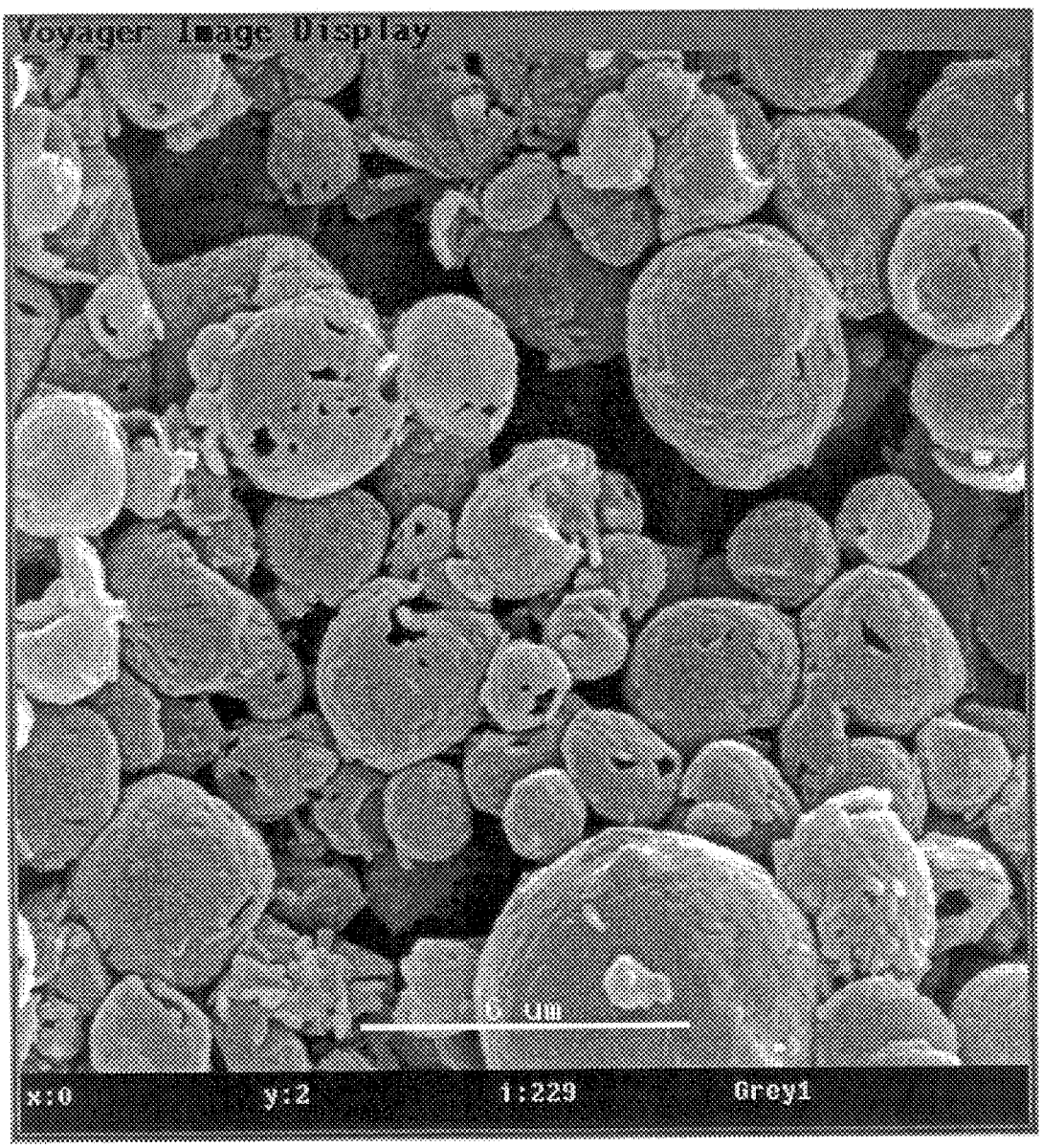
FIG. 1 is a SEM photograph of the microcapsules of the invention produced from tripalmitin.

The invention is based on the unexpected finding that a particularly useful solid microcapsule with a mean size from a fraction of micrometer to 1000 micrometers may be obtained when one or more biodegradable water insoluble, at room temperature solid, lipids are used to encapsulate a core which comprises air or a gas. Useful biodegradable lipids are solid water insoluble mono-, di- or tri-glycerides, fatty acids, fatty acid esters, sterols such as cholesterol, waxes and mixtures thereof. Mono-, di- and tri- glycerides include mainly the mono-, di- and tri-laurin compounds as well as the corresponding -myristin, -palmitin, -stearin, -arachidin and -behenin derivatives. Mono-, di- and tri-myristin, -palmitin -stearin and mixed triglycerides such as dipalmitoylmonooleyl glyceride are particularly useful; however, tripalmitin and tristearin are preferred. When made from fatty acids or mixtures of fatty acids with glycerides and/or sterols, the fatty acids include all, at room temperature solid, fatty acids (preferably saturated) having 12 carbon atoms or more. These fatty acids include, for instance, lauric, arachidic, behenic, palmitic, stearic, sebacic, myristic, cerotinic, melissic and erucic acids, the fatty acid esters. Preferably, the fatty acids and their esters are used in admixture with other glycerides.

The sterols are preferably used in admixture with the other glycerides and or fatty acids and are selected from cholesterol, phytosterol, lanosterol, ergosterol, etc. and esters of the sterols with the above mentioned fatty acids; however, cholesterol is preferred.

The best results in terms of yield of microcapsules and their general properties were obtained with triglycerides such as tripalmitin, tristearin or mixtures of the above mentioned triglycerides. Lower yields and microcapsules with a slight tendency to agglomeration were obtained when diglycerides were used. The lowest yields of microcapsules were obtained with monoglycerides. The exact explanation of such behaviour is unclear, however, it is postulated that the degree of hydrophobicity may be the reason which may explain the fact that the best microcapsules or microballoons are obtained from the fairly hydrophobic materials and as the hydrophobicity decreases or surface activity increases the quality and the quantity of the microcapsules obtained decreases. This is perhaps why in the experiments with mixtures of mono- di- and triglycerides (e.g. a mixture of mono-, di, and tripalmitin the yield steadily improves as the amount of triglyceride increases. The greater participation of the more hydrophobic triglyceride (lipid) the better microballoon's yield and the smoother the process of the manufacture.

Optionally, biodegradable water insoluble lipids may be admixed with up to 75% by weight of biodegradable polymers. The amount of biodegradable polymers is limited to 75% by weight, as it was surprisingly found that the biodegradability of the glyceride/polymer mixtures is not a linear function of the composition i.e. the biodegradability does not increase or decrease in direct proportion to the amount of the polymer present in the mixture, but that it is more determined or influenced by the biodegradability of the glycerides than by that of the polymers. This is so only as long as the amount of glycerides is equal to or greater than 25% by wt. as the mixtures containing 25% by wt. or more of the glyceride have biodegradability closer to that of lipids than to that of polymers. However, the mixtures with 75% by wt. or more of the polymer have biodegradability closer to that of pure polymers. This means that the mixtures with less than 25% of glycerides in terms of biodegradability will behave almost like the pure polymers. When, however, the amount of lipids approaches 25% the character of the mixture changes and further increase of the amount of lipids has a greater impact on the biodegradability of the mixture by imposing the lipid biodegradability rate to the polymers, i.e. rendering the mixture more biodegradable than what would or could be expected considering the amount of polymer present. This clearly demonstrates that biodegradability of the mixture is not a simple sum of the individual biodegradabilities but is conditioned by the component present in excess, however in such a way that the influence of the glycerides is predominant. For compositions with more than 75% by weight of the polymer, biodegradability rapidly approaches that of the pure polymer.

When prepared according to the invention, the glyceride containing hollow microcapsules with an average size between 1 $\mu$m and 1000 $\mu$m are prepared by dispersing, in a water carrier phase, a mixture of one or more of the solid constituents of the microcapsule envelope dissolved in an organic solvent, so as to produce an oil-in-water emulsion. The emulsion water phase may contain an effective amount of surfactants which are used to stabilise the emulsion. Surfactants such as polyvinyl alcohol (PVA), polyoxyethylene-polyoxypropylene block copolymers, phospholipids such as phosphatidic acid, phosphatidyl choline, phosphatidylethanol amine, phosphatidyl serine, phosphatidyl glycerol, phosphatidyl inositol and mixtures thereof, sorbitan ethers, sorbitan esters, polyoxyethylenesorbitan esters, ethoxylated saturated glycerides and partial fatty acid glycerides or polyglycerides, etc., but polyoxyethylene-polyoxypropylene block copolymers (e.g. Pluronic®, or Synperonic®) and phospholipids are preferred. Presence of the surfactants is compulsory only if the size of the final product or particle size distribution is important. If the microcapsules are used for a preparation intended for oral administration no surfactant (stabiliser) may be necessary as the final particle size is, practically, of no consequence. However, if the preparation is intended for parental administration, presence of the surfactant in the water phase is important. Prior to freezing at a temperature below −30° C., a certain amount of redispersing agent is added to the emulsion of tiny droplets of the organic solution in the water phase. The frozen emulsion is then subjected to reduced pressure to effect lyophilisation, i.e. the removal by sublimation of the organic solvent from the droplets and of the water of the carrier phase. It is postulated that during this relatively slow solvent removal, the membrane constituents migrate outwardly to the periphery of droplets until they arrive to the frozen water boundary where their further motion is impeded causing the formation of a molecularly organised dense deposit at the solvent/ice interface which may acquire a semi-crystalline structure in the area at the junction between the solvent and the ice, i.e. at the solvent to ice interphase. In this manner, the membrane constituents assemble into at least partly non amorphous, dense structure of significant strength, and reduced porosity which may explain the unusually favourable properties of the present microcapsules.

Any convenient redispersing agent may be used; however redispersing agents selected from albumin, gelatine, polyvinyl pyrolidone (PVP), polyvinyl alcohol (PVA), polyethylene glycol (PEG) and polyoxyethylene-polyoxypropylene block copolymer (e.g. Pluronic®, or Synperonic®) are preferred. The redispersing agents which are added to prevent particle agglomeration are particularly useful when the microcapsules are in the form of non-coalescent, dry and instantly dispersible powders. Produced for a long storage or from hydrophobic triglyceride materials such as tripalmitin or tristearin, the microcapsules preparations of the invention further comprise one or more redispersing agents.

The porosity of the hollow microcapsules made according to the invention is usually very low and sometimes the microcapsules have no pores at all. It appears that the porosity is a function of the lipid concentration or wall thickness of the microcapsule. When porous, the microcapsules of the invention have the pore size in the range of 20 to 2,000 nm.

As already mentioned when the microcapsules of the invention are prepared from mixtures of one or more biodegradable water insoluble lipids with biodegradable polymers, up to 75% by weight of the polymer may be used. Microcapsules made from biodegradable lipids may, upon administration, last in the body from about 1 hour to several hours, whereas the biodegradable polymers may last several days or several weeks. Hence, microcapsules of controlled half-life after administration can be customised by adjusting the respective proportions of the lipids and biodegradable polymers during fabrication. The exact amount of the polymer will depend on the application and will be directly related to the degree of biodegradability required. For example, for certain sustained release applications the amount of biodegradable polymer may be anywhere between 30% and 60% by wt. and in some cases up to 75% by weight. However, if the microcapsules of the invention are used for echographic imaging of organs and tissue, depending on the desired rate of clearance from the body, the amount of biodegradable polymer may be between 1–50% by wt. preferably between 0.5–10% by wt. or as low as 0.1% by wt. Obviously, for certain applications, such as imaging of the liver or spleen or echocardiography, the imaging may be carried out with aqueous suspensions of microcapsules (microballoons) containing the microcapsules made out of pure glycerides e.g. pure tristearin and pure tripalmitin, or pure mixed triglycerides like dipalmitoylmonooleyl glyceride or glyceride/fatty acid/sterol mixtures.

The microcapsules used for echography typically having relatively thin walls e.g. 50–500 nm thick are particularly advantageous as their biodegradability is very rapid i.e. that the clearance of the lipidic envelopes from the body, occurs within a relatively short period of time e.g. maximum 24 hours. For the known microballoons this is very rapid so that, in terms of response in the organism, the ultrasonic contrast agents of the invention may be compared to contrast agents comprising aqueous gas microbubble suspensions in which the microbubbles are bound by a liquid/gas interface, i.e. have no tangible material envelope. In such suspensions, the gas liquid interface is stabilised by surfactants, typically phospholipids, dispersed in the liquid carrier. Thus it follows that the microcapsules of the invention provide unique contrast agents with microballoons of useful and controled "life cycle". The agent in which the microballoons have the required stability for their delivery to the desired sites and sufficient biodegradability so that upon echographic imaging their elimination from the body is rapid.

When microcapsules are made from mixtures of one or more water insoluble lipids with a biodegradable polymer the polymer used is selected from partially esterified polyamino-acids, polylactic and polyglycolic acid and their copolymers, copolymers of lactides and lactones, polypeptides, poly-(ortho)esters, polyglutamic acid, polyaspartic acid, and their copolymers, poly-β-aminoketones, polyphosphazenes, polyanhydrides, polyhydroxy-butyrate, polyamides, polydioxanone, poly(DL-lactide-co-δ-caprolactone), poly(DL-lactide-co-δ-valerolactone) and polyalkyl-(cyano)acrylates, however, polylactides and polyglycolides and their copolymers are preferred. When it is desirable to impart some particular properties of polymers onto the desired composition, for instance, bioadhesivity other non-biodegradable polymers such as ethylenevinyl acetate, polyacrylic acid, etc. may also be used alone or in admixture with the above mentioned biodegradable polymers.

The microcapsules of the invention may be used for the delivery of therapeutically active substances, in which case the active substance may be included in the membrane or may be loaded in the core. The substances which are lipophilic are particularly suitable for incorporation into lipidic or lipidic/polymeric membrane material. The amount of lipophilic active material incorporated into the membrane will depend on the nature and the molecular weight; however, very high active substance to lipid ratios are obtained when lipophilic substances such as vitamin E, prednisolone, chloramphenicol palmitate and salbutamol are used. Virtually any biologically active substance can be used with the microcapsules according to the invention. Such substances include but are not limited to, antibacterial compounds such as gentamycin, antiviral compounds such as rifampacin, antifungal compounds such as amphotericin B, antiparasitic compound such as derivatives of antimony, antineoplastic compound such as mitomycin C, doxorubicin and cisplatinum, contraceptives such as norgestrel, steroids such as spironolactone, estradiol, glucocorticoids such as prednisolone, fluorescent compounds such as carboxy fluoroscein, anti-inflammatories such as salicylic acid and ibuprofen, anesthetics such as bupivacaine, lidocaine, etc. Particularly, good results are obtained when the microcapsules are used for administration of antibacterial antineoplastic compounds.

Experiments have shown that when the microcapsules of the invention are used as delivery vehicles for active substances, different effects may be achieved by varying the concentration of the lipid or lipid/polymer mixture in the starting material. It has been established that microcapsules with relatively thin walls and a high active substance to lipid or lipid/polymer ratio, i.e. high concentration of the active ingredient, will produce a shock treatment in the surrounding tissue. A particular advantage of the microcapsules of the invention comes from the fact that the shock treatment may be customised by varying the ratio or the wall thickness while maintaining the concentration of the active substance at a constant level thus producing a form of sustained release system. The system in turn may be fully adapted to the substance carried, the treatment envisaged and even the physiological condition of the patient. Those skilled in the art will recognise that the degree of the freedom that the system of the invention provides is without comparison.

Further advantage of the microcapsule of the invention may be demonstrated by the possibility and ease of manufacture of the so called floating capsules. Recently introduced the floating capsules are intended for oral administration of drugs which are advantageously released while the capsule is floating in the gastric juices. Typical applications for such capsules are applications in which oral administration is preferred. Due to the fact that the microcapsules of the invention have a core which is filled with gas it makes the microcapsules ideal candidates for the production of systems where administration of active substances requires "floating" conditions. Whether packed as a powder in a large polymeric capsules or processed conveniently into tablets, the microcapsules provide for floating action.

Injectable compositions comprising a suspension of an effective amount of microcapsules in a pharmaceutically acceptable liquid carrier with usual additives and stabilisers are also part of the invention.

The invention also concerns a method of making solid microcapsules, by dissolving one or more biodegradable water insoluble, at room temperature solid, lipids and optionally a biodegradable polymer in an organic solvent or a solvent mixture, admixing with an aqueous phase, emulsifying the mixture to form an oil-in-water emulsion, adding a redispersing agent, freezing the mixture, lyophilising in the presence of air or a gas to form a powder containing air or gas filled semi-spherical or spherical microcapsules, dispersing the powder in an aqueous carrier, separating the air or gas containing microcapsules from debris by decantation, and drying the recovered microcapsules.

Depending on the exact composition of the membrane as for example when mixtures with biodegradable polymers are used, the above method may be modified to include additional evaporation of the organic solvent. The evaporation then may be carried out after formation of the oil-in-water emulsion. When the microcapsules carry a liposoluble physiologically active substance, the substance is added to the organic solution of the membrane forming material prior to contacting with the aqueous phase.

The organic solvents used to prepare the lipid solutions may be pure or mixtures of solvents. In case of mixtures, depending on the type and the amount of biodegradable polymer, the mixture may include water soluble and water insoluble organic solvents. The water insoluble organic solvents are selected from alkanes, cycloalkanes, aromatic hydrocarbons, ethers and halogenated hydrocarbons. More specifically the solvent may be selected from toluene, xylene, cyclooctane, cyclohexane, chloroform, tetrachloro methane, difluorotetrachloro ethane, dibutyl ether, diisopropyl ether, isobutyl-methyl ketone and their mixtures.

Any water soluble solvent may be used but tetrahydrofuran (THF) is preferred. To ensure smooth operation, the aqueous phase may be saturated with THF prior to admixing with the organic solution. Clearly, the aqueous phase may further contain different amounts of ionic or non-ionic surfactants which serve to stabilise the emulsion. If upon formation the oil-in water emulsion is rapidly frozen no surfactant may be necessary. Any of the known surfactants may be used however polyoxyethylene/polyoxypropylene block copolymers and phospholipids are preferred.

The microcapsules of the invention may be loaded with several active substances at the same time. As already mentioned the capsule may carry a physiologically active ingredient in the membrane but it may also carry an active substance in the core itself. From active substances carried in the core the following compounds are contemplated insulin, peptides, polypeptides, immunomodulators, hormones, enzymes and enzyme inhibitors, heparin, blood proteins, nucleotides, saccharides, morphine, proxyphylline, ionic and non-ionic iodinated contrasts agents including iopamidol, iomeprol and the like, MRI contrast agents such as gadolinium complexes with various chelating agents including Gd-BOPTA, Gd-DTPA, Gd-EDTA, etc., however, insulin and iomeprol are preferred. When the core is filled with air or a gas and the membrane is made of pure lipid or a mixture of lipids containing up to 75% by wt. of biodegradable polymers, the microcapsules of the invention are suitable for echographic imaging of organs of human or animal body. Obviously, the exact microcapsule composition in this case will depend on the desired clearance of the microcapsules from the body. Echographic contrast agents are easily produced by suspending the microcapsules of the invention in a suitable physiologically acceptable aqueous carrier such as buffered or unbuffered physiological saline solution (0.9% aqueous NaCl; buffer 10 mM tris-HCl) or a 5% aqueous dextrose or mannitol solution or a 2.6% aqueous glycerol solution. When the manufacture of injectable therapeutically effective compositions comprising the microcapsules of the invention are contemplated, the microcapsules carrying active ingredients are suspended in the commonly used physiologically acceptable carriers containing usual additives and stabilisers.

The following examples further illustrate the invention:

EXAMPLE 1

Various amounts of tripalmitin (see table) were dissolved in carbon tetrachloride (0.6 ml) and the resulting solutions were emulsified in distilled water (40 ml) containing 0.1% SYNPERONIC F108 (ICI) using a POLYTRON homogeniser (10000 rpm, 1 min). The average diameter of the resulting droplets was 4 µm as determined with a photon correlation spectrometer (Malvern Master Sizer).

This emulsion was added to a 500 ml glass vessel containing 250 mg of bovine serum albumin (from SIGMA) dissolved in 10 ml of distilled water. After mixing, the resulting solution was rapidly cooled at −40° C. and lytophilised (CHRIST). After lyophilisation, the cake was resuspended in 12 ml of distilled water. Air-containing microcapsules rose to the surface while debris, broken shells, etc. remained in solution or sunk to the bottom of the container. The floating capsules recovered, were resuspended in 0.9% NaCl and aliquots of the microcapsules analysed by Scanning Electron Microscopy (SEM). Spherical microcapsules with average size of 4 µm and in some cases with visible pores were observed (see FIG. 1). The porous microcapsules were often present at concentrations of tripalmitin about 50 mg or less. At higher concentrations of tripalmitin i.e. more then 50 mg flakes of tripalmitin were observed on the surface of the microcapsules. To determine average wall thickness a number of microcapsules were placed between two glass plates and broken. The thickness was then estimated by SEM.

TABLE 1

| Tripalmitin added (mg) | Approximate wall thickness (nm) | Total microcapsules formed (in $10^7$/ml) |
|---|---|---|
| 10 |  | 0.1 |
| 30 | 70 | 6.0 |
| 50 | 70–100 | 26 |
| 75 | 160 | 48 |
| 100 | 300 | 89 |
| 200 | 300–500 | 80 |

Thus with increasing amounts of tripalmitin, the wall thickness of the microcapsules and with it the yield of intact (i.e. floating) microcapsules also increase.

Figure 2:
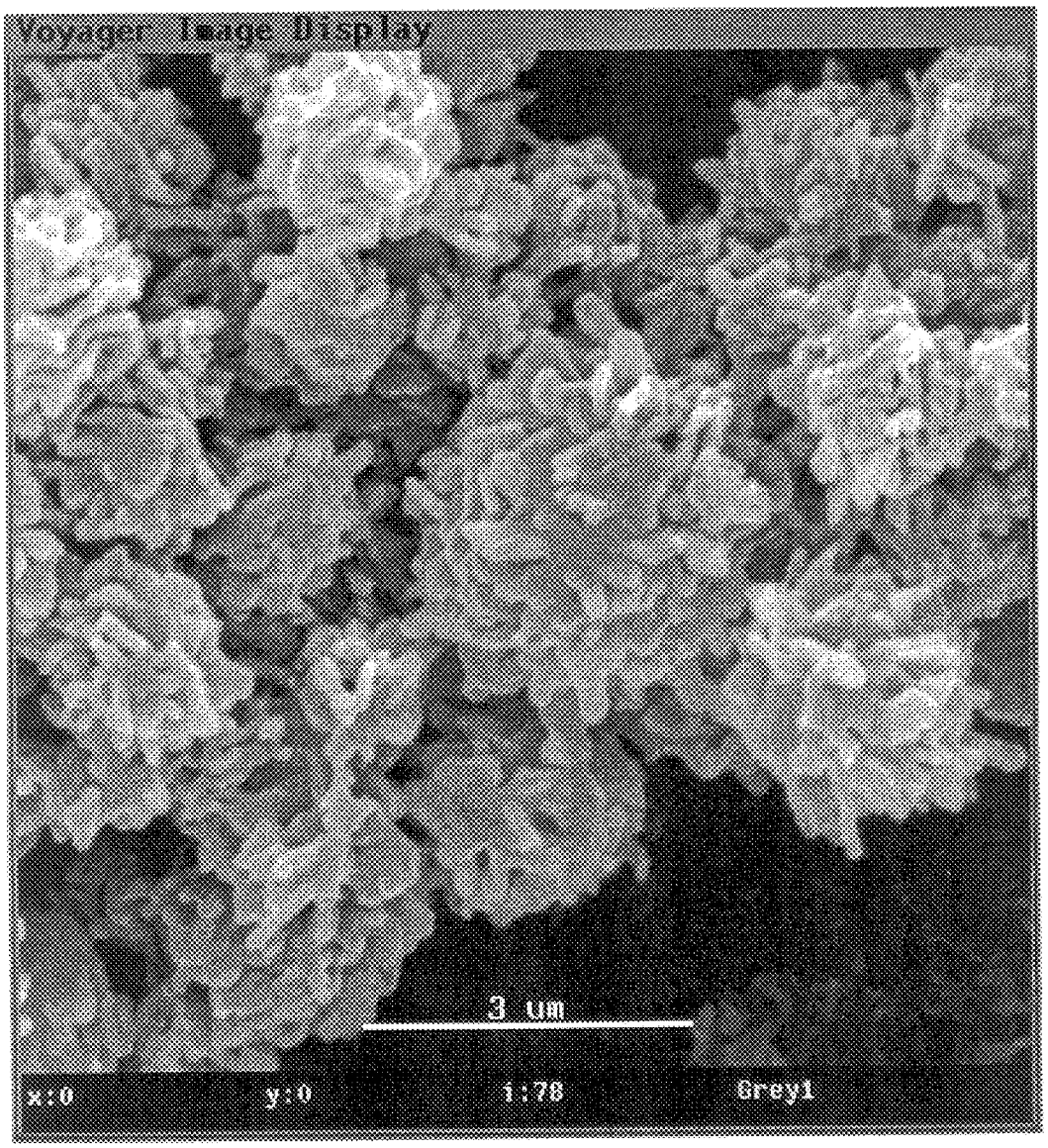
FIG. 2 is a SEM photograph of the tripalmitin deposit obtained by evaporation of the organic solvent.

If the above example is repeated but instead of lyophilisation the emulsion obtained is placed in a rotary evaporator and the organic solvent is slowly evaporated the resulting cake will be in the form of crystal-like deposit of solid tripalmitin particles (see FIG. 2).

EXAMPLE 2

The experiments of Example 1 were repeated using other biodegradable lipids and/or solvents. Floating microcapsules were obtained with triglycerides (triarachin, tristearin, tripalmitin, trimyristin, trilaurin), mixed triglycerides (distearoylmonooleylglyceride), diglycerides (dipalmitin), fatty acids (palmitic acid, stearic acid), cholesterol esters (cholesterol palmitate) and waxes (such as myricyl palmitate). Commercial lipid preparations such as hydrogenated vegetable oil (Lutrilab) or saturated polyglycolysed glycerides (Gelucire, Gattefosse, France) may also be used. The following water insoluble solvents gave satisfactory results: toluene, xylene, cyclooctane, cyclohexane, difluorotetrachloroethane, dibutylether, diisopropylether, chloroform, isobutyl methylketone. As redispersing agent, bovine serum albumin, polyvinyl alcohol, polyethyleneglycol and block copolymers of oxyethylene/oxypropylene (poloxamers, Pluronic® or Synperonic®) are particularly effective.

EXAMPLE 3

Example 1 was repeated by replacing carbon tetrachloride by a mixture of water soluble and water insoluble solvent such as cyclooctane (0.6 ml) and tetrahydrofuran THF (30 ml). Under these conditions, a mechanical agitation (at 1000 rpm) was sufficient to produce a stable emulsion without the need for a homogenizer. Prior to the lyophilisation, most of the THF was removed by evaporation at 15° C. (30 min, 15 mm Hg) in a rotary evaporator. Floating microcapsules were obtained using dipalmitin, tristearin, tripalmitin, palmitic acid and stearic acid.

Mixtures of lipids gave also good yields of floating microcapsules for instance tripalmitin with 5–40% (w/w) of one of the following lipids: triundecanin, cholesterol, palmitic acid, sebacic acid, monopalmitin and dipalmitin.

EXAMPLE 4

Microcapsules made of a combination of lipids and biodegradable polymers were obtained using the procedure described in Example 3. For instance polylactic-co-glycolic acid (RESOMER R207 from Boehringer Ingelheim, Germany), polyphosphazene, esters of polyglutamic acid. Biodegradability measurements of microcapsules made from pure glycerides have shown that the microcapsules containing no polymer were completely digested within 24 hours. Although there was a difference in biodegradability between various glycerides (dipalmitin, tripalmitin and tristearin) this difference was small in comparison to the results obtained for the mixtures of glycerides with biodegradable polymers.

Microcapsules were prepared as described in Example 3, using various ratios of tripalmitin to polyglutamic acid esters. The polymer used was esterified with isoamyl alcohol (degree of esterification 65%), and labelled with a trace amount of $^{14}C$ ethanol (Du Pont-NEN). The capsules made of pure tripalmitin were labelled with $^{14}C$ tripalmitin (Amersham). The mean diameter of the microcapsules was between 3.5 and 4.5 μm. The microcapsules were suspended in saline and injected intravenously to mice. ($6 \times 10^9$ microcapsules/kg). Groups of three mice were sacrificed after 3 days (72 hours), 28 days (672 hours) and 90 days (2160 hours). Since the microcapsules were primarily taken up by the liver, biodegradability of the microcapsules was measured by counting the total radioactivity of the liver. The results (see Table 2) show in all cases a major uptake of the injected radioactivity in the liver after 3 days. In the case of the 100% tripalmitin capsules, after 3 days, the capsules were digested and the degradation products were eliminated. On the other hand the polymer containing capsules were degraded more slowly. With 75% or 50% tripalmitin the capsules are largely digested after 28 days while the capsules with 25% tripalmitin behave almost as pure polymeric microcapsules. Similar results were obtained with tristearin/polylactic-coglycolic acid microcapsules.

Analysis of the results shows that biodegradability is not a linear function of the composition i.e. that biodegradability does not increase or decrease in the direct proportion of the amount of the less biodegradable component (the polymer) but that biodegradability of the composition is dominated or determined more by the biodegradability of glycerides than those of the polymers. This is particularly so in the range between 100%–25% of glycerides or between 0–75% by wt of the biodegradable polymer.

TABLE 2

| Tripalmitin/ Polyglut. acid | % of the injected dose in liver after | | | |
|---|---|---|---|---|
| % by wt. | 1 hr. | 72 hrs. | 672 hrs. | 2160 hrs. |
| 100/0* | 38 | 2 | 0 | 0 |
| 87.5/12.5 | 52 | 18 | 3 | 0 |
| 75/25 | 67 | 70 | 11 | 1 |
| 50/50 | 76 | 76 | 31 | 4 |
| 25/75 | 71 | 73 | 57 | 18 |
| 0/100 | 73 | 75 | 65 | 15 |

*The capsules were labelled with $^{14}C$ tripalmitin. In all other cases the polymer was labelled.

This means that the glycerides in the amount of over 25% have a greater impact on the biodegradability of the mixture that they impart their biodegradability to the polymers rendering the mixture more biodegradable than what could or would be expected considering individual amounts of present. This clearly demonstrates that biodegradability of the mixture is not a simple sum of individual biodegradabilities but conditioned by the component present in excess, however in such a way that influence is shifted towards biodegradability of glycerides. For compositions with more than 75% by weight of the polymer biodegradability rapidly approaches that of the pure polymer.

EXAMPLE 5

Microcapsules containing diazepam (7-chloro-1,3-dihydro-1-methyl-5-phenyl-2H-1,4-benzodiazepin-2-one, Valium®, Roche) were prepared as described in Example 1 using 15 mg of diazepam and 85 mg tripalmitin. After formation of the emulsion by mechanical agitation in an aqueous medium containing 0.1% polyvinyl alcohol (PVA), the preparation was cooled to −40° C. and lyophilised. The resulting cake was resuspended in water in order to recover only the floating capsules. The floating (air filled) capsules were collected and dried. The yield expressed as diazepam recovered was 42%. The capsules exhibited a broad range of sizes from 5 μm up to more than 100 μm. In vitro the "floating capsules" showed to release the drug gradually and regularly in the aqueous medium over a period of 12 hours. From the above results it may be expected that the drug-containing floating microcapsules according to the invention after oral administration, will remain in the stomach for extended periods of time (for instance 9 hours) releasing slowly and continuously the entrapped drug. By comparison a regular non-floating tablet containing the free drug dissolves instantly in which case it delivers "an overdose" of the drug. However, if its dissolution is slowed then it is eliminated from the stomach within the normal transit times i.e. at the most within two hours after administration. Thus the microcapsules of the invention provide an advantage over normal or non-floating microcapsules or particles.

EXAMPLE 6

Microcapsules were prepared as described in Example 1 using on one hand 5 mg of tetracaine (base form, SIGMA) and 30 mg of tristearin and on the other hand 5 mg of tetracaine and 50 mg of tristearin. The two preparations yielded microcapsules with similar average size (diameter) of 4.5 $\mu$m but different wall thickness. The preparation with 30 mg of tristearin formed "thin-walled" (60–70 nm) microcapsules and 50 mg of tristearin "thick-walled" (80–100 nm) microcapsules. The entrapment yield of tetracaine was respectively 30% and 50%. The drug release properties of thin-walled and thick-walled microcapsules were compared. Equal amounts of thin-walled and thick-walled microcapsules were suspended in 10 ml of 0.9% NaCl. The samples were then introduced into dialysis bags (MW cut of 15'000) and the bags were suspended in 40 ml of 0.9% NaCl. Aliquots of the dialysate (100 $\mu$l) were collected at different times mixed with 1 ml of aqueous THF (60%) and the release of tetracaine determined as a function of time by UV spectrophotometry at 307 nm. Thin-walled microcapsules showed a very fast release as 75% of the entrapped drug was liberated after 8 hours whereas for thick-walled microcapsules only 53% of the drug was released after 8 hours. The difference (or slowdown) of 22% in release of the drug for the microcapsules with such a small difference in the wall thickness is considered that a large span of drug release may be obtained by further adjustments in the wall thickness of the microcapsules. Thus by controlling the wall thickness it is possible to control and adjust the release of a drug to a desired value.

EXAMPLE 7

Example 1 was repeated by incorporating different drugs in addition to the biodegradable lipid. Good results were in particular obtained with vitamin E, prednisolone, chloramphenicol palmitate, norgestrel and salbutamol.

EXAMPLE 8

The potential use of the microcapsules prepared in Example 1 as contrast agent for echography was assessed by measuring the backscatter coefficient at 7 MHz of suspensions containing $7 \times 10^5$ microcapsules per ml.

Figure 3:
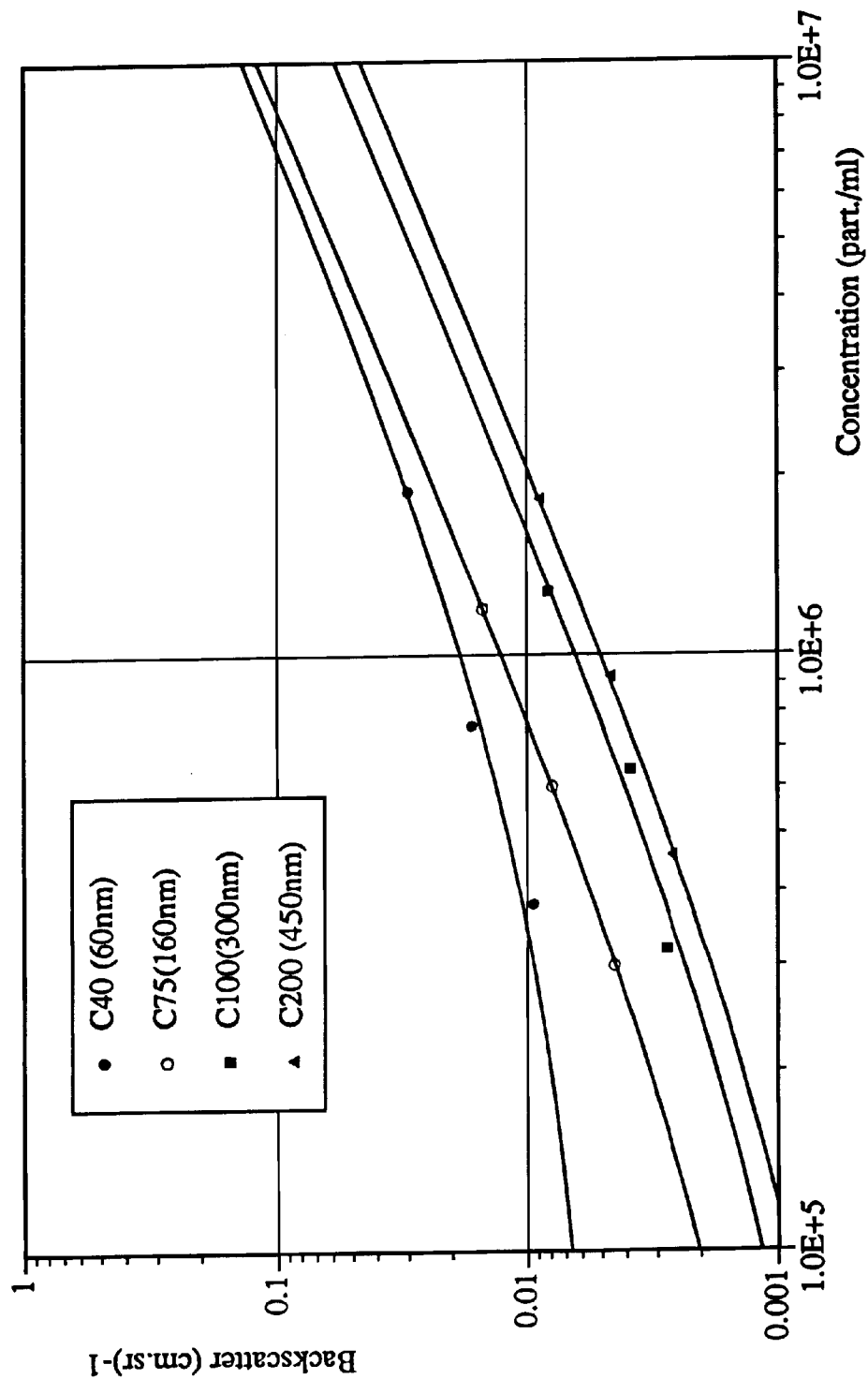
FIG. 3 is a graphical representation of changes in echogenicity of the microcapsules as a function of wall thickness.

As seen from the Table 3 and FIG. 3, the thinner the microcapsule wall (i.e. microcapsules prepared with low amounts of tripalmitin) the

TABLE 3

Figure 4:
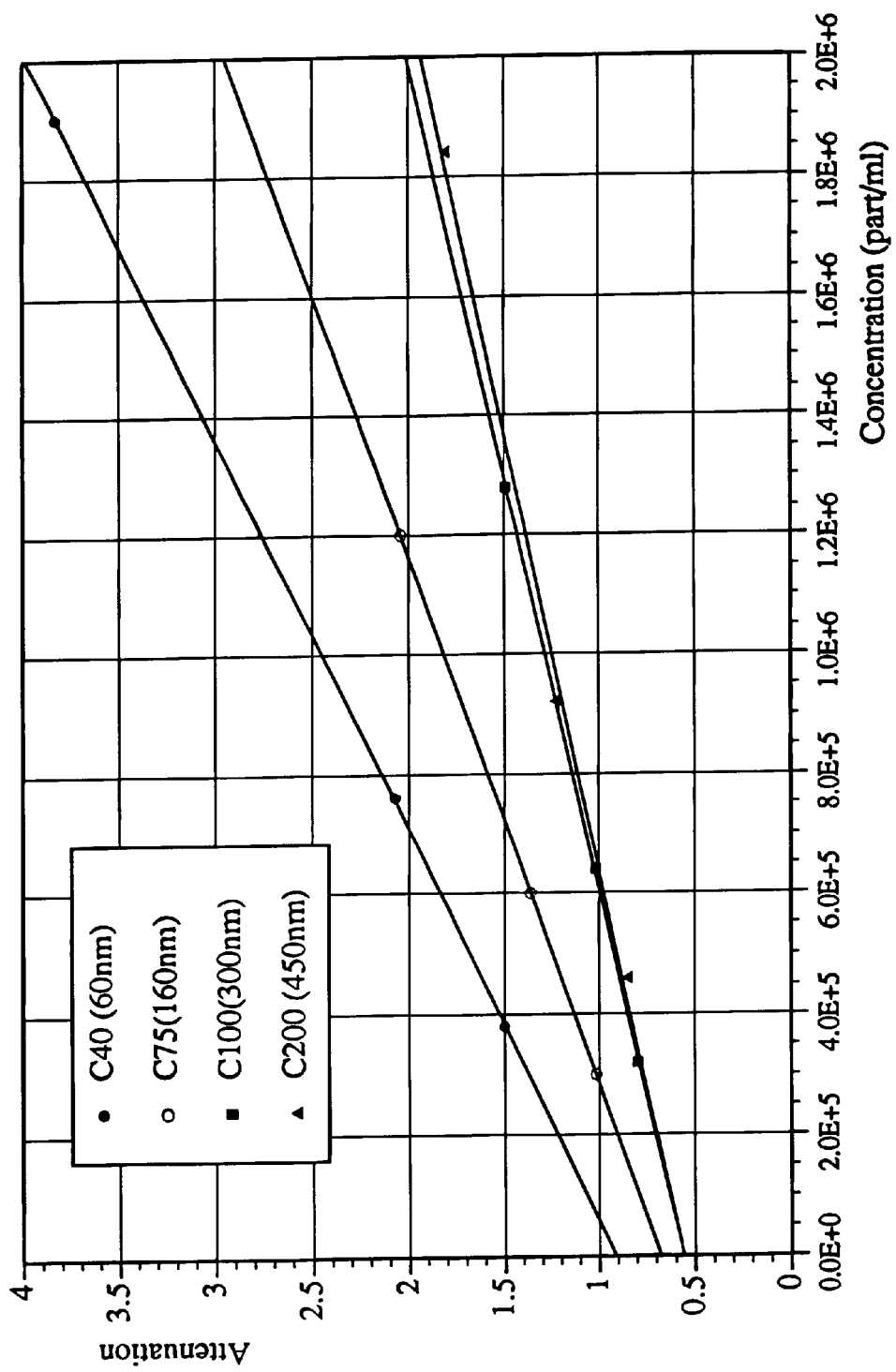
FIG. 4 is a graph of change in echographic signal attenuation as a function of the microcapsule wall thickness and concentration.

| Tripalmitin added (mg) | Backscatter coefficient ($cm^{-1} \cdot sr^{-1}$) |
| --- | --- |
| 40 | 0.013 |
| 75 | 0.009 |
| 100 | 0.0041 |
| 200 | 0.0033 | higher the echogenicity. With an increase in wall thicknesses e.g. from 60 nm (C40 in FIG. 3) to 160 nm (C75 in FIG. 3) and further to 300 nm (C100 in FIG. 3 obtained with 100 mg of tripalmitin or more (C200 in FIG. 3) the echogenicity decreases. At concentrations of more than 100 mg and wall thickness of about 90 nm it becomes very low indicating that the microcapsule walls are becoming too rigid for effective and efficient response to the pressure changes induced by ultrasonic vibrations. This becomes particularly evident when the attenuation in echographic signal is ploted as a function of the microcapsule wall thickness and concentration of the microcapsules in the suspension (see FIG. 4). From the graph it follows that the signal attenuation is linear function of the wall thickness and that by decreasing the wall thickness of the microcapsules by 50% the attenuation of the echographic signal increases two fold.

EXAMPLE 9

100 mg of dried microcapsules with the wall thickness between 50 nm and 100 nm were produced according to Example 1. 1.3 mg of the capsules were dispersed in 2 ml of physiological saline solution. The suspension gave a strong echographic signal in the renal artery for two hours in pulsed and colour Doppler mode after intravenous injection to the rabbit.

The same experiment was repeated with microcapsules prepared according to Example 3 using a mixture with 30, 50 and 75% of polylactic-co-glycolic acid. The microcapsules were suspended in aqueous saline solution and intravenously injected into the rabbit. The echographic responses obtained for the three samples were equally effective.

EXAMPLE 10

Thin-walled microcapsules were prepared as described in Example 1 using 50 mg tripalmitin. The microcapsules (about 4 $\mu$m) recovered after lyophilisation and decantation in saline (5 ml, $6 \times 10^8$ microcapsules per ml) were introduced in a 50% aqueous solution of iomeprol (a non ionic iodinated contrast agent developed by BRACCO, Italy) in a pressure tight container. The empty microcapsules were filled with the aqueous contrast agent solution by applying a pressure of 2–4 bars during 1 min whereby the microcapsules sunk. The filled microcapsules were then recovered by slow centrifugation, resuspended in a small amount of distilled water containing 10 mg/ml of albumin and dried. The resulting powder was resuspended in distilled water and the floating microcapsules recovered. This was repeated several times until all non-encapsulated iomeprol was eliminated. The analysis of the entrapped iomeprol was performed by submitting aliquots of the preparation to a high pressure (typically 4 bars), incubating for 1 hour at room temperature and then measuring the iomeprol released by UV spectrophotometry. The results showed encapsulations of 0.5–2 mg of iomeprol per mg of dried microcapsules. Considerable enhancement of the liver contrast was observed by computed tomography after intravenous injection to the rat of a 0.9% NaCl solution containing 40 mg (dry weight) of the iomeprol-filled microcapsules. Insulin-filled microcapsules were prepared in a similar way and an even higher load was achieved. These examples show that it is possible to fill the microcapsules of the invention with hydrophilic compounds.

What is claimed is:

1. A solid microcapsule for use in ultrasound echography with a mean size from a fraction of micrometer to 1000 micrometers, the microcapsule having a biodegradable, 50 to 500 nm thick solid membrane encapsulating an air or a gaseous core, wherein the solid membrane consists essentially of the membrane-forming constituents:

(a) one or more biodegradable, water insoluble and at room temperature solid triglycerides, and, optionally (b) up to 75% by weight of a biodegradable polymer.

2. A solid microcapsule for use in ultrasound echography with a mean size from a fraction of micrometer to 1000 micrometers, the microcapsule having a biodegradable, 50 to 500 nm thick solid membrane encapsulating an air or a gaseous core, wherein the solid membrane comprises, as the membrane-forming constituents:

(a) one or more biodegradable, water insoluble and at room temperature solid triglycerides, and, optionally (b) up to 75% by weight of a biodegradable polymer, wherein the solid membrane is biodegradable and after being administered for ultrasound echography is cleared from a body in 24 hours or less.

3. A solid microcapsule for use in ultrasound echography with a mean size from a fraction of micrometer to 1000 micrometers, the microcapsule having a biodegradable, 50 to 500 nm thick solid, at least partially non amorphous, dense membrane encapsulating an air or a gaseous core, wherein the solid membrane is a tangible, material envelope consisting essentially of as the membrane-forming constituents:

(a) one or more biodegradable, water insoluble and at room temperature solid triglycerides, and, (b) 0.1 to 75% by weight of a biodegradable polymer.

4. A solid microcapsule for use in ultrasound echography with a mean size from a fraction of micrometer to 1000 micrometers, the microcapsule having a biodegradable, 50 to 500 nm thick solid, at least partially non-amorphous, dense membrane encapsulating an air or a gaseous core, wherein the solid membrane is a tangible, material envelope consisting essentially of the membrane-forming constituents:

(a) one or more biodegradable, water insoluble and at room temperature solid triglycerides, and, optionally (b) up to 75% by weight of a biodegradable polymer.

5. The microcapsule of claim 1 wherein the tri-glyceride is tri-myristin, palmitin or stearin, or mixtures thereof.

6. The microcapsule of claim 1, where in the membrane is at least partly crystalline or semi-crystalline.

7. The microcapsule of claim 1 wherein the membrane comprises up to 10% by wt of biodegradable polymers.

8. The microcapsule of claim 1 wherein the microcapsule has an average size distribution between 0.1 $\mu$m and 100 82 m.

9. The microcapsule of claim 1, wherein the microcapsule is porous and has a porosity of 20 to 2,000 nm.

10. The microcapsule of claim 1, wherein the microcapsule is non-coalescent, dry and instantly dispersible in a liquid carrier.

11. The microcapsule of claim 10, wherein the microcapsule further comprises a redispersing agent.

12. The microcapsule of claim 11, wherein the redispersing agent is selected from albumin, polyvinyl alcohol, and polyethylene glycol.

13. The microcapsule of claim 7, wherein the biodegradable polymer is present in an amount of between 0.5–10% by wt.

14. The microcapsule of claim 1, wherein the biodegradable polymer is selected from polyamino acids, polylactides and polyglycolides and their copolymers, copolymers of lactides and lactones, polypeptides, poly-(ortho)esters, polydioxanone, poly-$\beta$-aminoketones, polyphosphazenes, polyanhydrides, polyhydroxy-butyrate and polyalkyl-(cyano)-acrylates.

15. The microcapsule of claim 1, wherein the microcapsule further comprises a surfactant selected from polyoxyethylene-polyoxypropylene block copolymers and phospholipids.

16. The microcapsule of claim 1, wherein the membrane further comprises a lipophilic active substance.

17. The microcapsule of claim 16, wherein the lipophilic active substance is selected from vitamin E, prednisolone, chloramphenicol palmitate and salbutamol.

18. A method of making an ultrasound contrast agent by suspending the microcapsules of claim 1 in a physiologically acceptable carrier phase.

19. Injectable composition comprising a suspension of an effective amount of microcapsules of claim 1 in a pharmaceutically acceptable liquid carrier with additives and stabilizers.

20. The microcapsule of claim 5, wherein the tri-glyceride is tripalmitin or tristearin.

21. The microcapsule of claim 1, wherein the biodegradable polymer is present in an amount of up to 20% by wt.

* * * * *